United States Patent

Atkins et al.

[11] Patent Number: 6,005,146
[45] Date of Patent: Dec. 21, 1999

[54] STABILIZED NON-POLYMERIC ACETOACETATE ESTERS THAT PROMOTE ADHESION TO METALLIC AND OXIDIZED SUBSTRATES

[75] Inventors: Douglas Grant Atkins; Jonathan Stewart Witzeman, both of Kingsport, Tenn.

[73] Assignee: Eastman Chemical Company, Kingsport, Tenn.

[21] Appl. No.: 09/197,305

[22] Filed: Nov. 20, 1998

Related U.S. Application Data

[62] Division of application No. 08/944,654, Oct. 6, 1997, Pat. No. 5,913,970.

[51] Int. Cl.$^6$ .................................................. C07C 211/00
[52] U.S. Cl. ..................... 564/511; 564/468; 564/469; 564/504; 564/509; 564/512
[58] Field of Search ..................... 564/511, 512, 564/468, 469, 509, 504, 474, 489

[56] References Cited

U.S. PATENT DOCUMENTS

| | | | |
|---|---|---|---|
| 3,668,183 | 6/1972 | Hoy et al. | 528/228 |
| 4,296,226 | 10/1981 | Braun et al. . | |
| 4,421,889 | 12/1983 | Braun et al. . | |
| 5,002,998 | 3/1991 | Carey et al. . | |
| 5,017,649 | 5/1991 | Clemens | 525/59 |
| 5,055,511 | 10/1991 | Ingle . | |
| 5,120,607 | 6/1992 | Ingle . | |
| 5,151,470 | 9/1992 | Sanders et al. | 525/407 |
| 5,266,630 | 11/1993 | Noomen et al. | 524/714 |
| 5,288,804 | 2/1994 | Kim et al. | 525/154 |
| 5,342,882 | 8/1994 | Gobel et al. | 524/832 |
| 5,349,026 | 9/1994 | Emmons et al. | 525/328.6 |
| 5,426,148 | 6/1995 | Tucker | 524/496 |
| 5,459,178 | 10/1995 | Chan et al. | 523/139 |
| 5,494,975 | 2/1996 | Lavoie . | |
| 5,714,563 | 2/1998 | DePompei et al. | 528/59 |

FOREIGN PATENT DOCUMENTS

| | | |
|---|---|---|
| 26982 | 4/1981 | European Pat. Off. . |
| 0 326 723 A1 | 8/1989 | European Pat. Off. . |
| 0 390 370 A1 | 10/1990 | European Pat. Off. . |
| 0 599 478 | 6/1994 | European Pat. Off. . |
| 4-164873 | 6/1992 | Japan . |

OTHER PUBLICATIONS

Chemical Abstracts, vol. 113, No. 12, Sep. 17, 1990, Columbus, Ohio, US; abstract No. 103487, Nishijima Keiji: "gamma–ray–resistant vinyl chloride polymer compositions for medical goods" XP002065407 see abstract & JP 02 080 451 A (Kyodo Yakuhin) Mar. 20, 1990.
English abstract of JP 3,290,486 (No Date).

*Primary Examiner*—Diana Dudash
*Attorney, Agent, or Firm*—Rose M. Allen; Harry J. Gwinnell

[57] ABSTRACT

The present invention provides improved adhesion promoters for latex paints. The adhesion promoters are enamines of acetoacetate esters, or substituted acetoacetate esters. The invention also provides two new compounds which are useful as adhesion promoters: 2-butyl-2-ethyl-1,3-propanediol bis(3-amino-2-butenoate) and trimethyl propane tris(3-amino-2-butenoate), and which are stable to hydrolysis on prolonged storage.

2 Claims, No Drawings

STABILIZED NON-POLYMERIC ACETOACETATE ESTERS THAT PROMOTE ADHESION TO METALLIC AND OXIDIZED SUBSTRATES

This is a Divisional application of application Ser. No. 08/944,654, filed Oct. 6, 1997, now U.S. Pat. No. 5,913,970.

FIELD OF THE INVENTION

The present invention is directed to waterborne coating compositions containing an aqueous polymer dispersion and a non-polymeric material which improves adhesion to metal substrates.

BACKGROUND OF THE INVENTION

Waterborne coatings comprise a polymeric material dispersed or dissolved in an aqueous medium. When a waterborne coating is applied to a substrate and dried, the polymeric material forms a film which protects the substrate. Certain additives such as coalescing agents or plasticizers are frequently used to promote coalescence of the latex particles in the coating during film formation so that the resulting film has a smooth glossy appearance and completely covers and protects the substrate. Other additives are used to improve the adhesion of the coating film, especially on metal substrates.

U.S. Pat. Nos. 4,296,226 and 4,421,889 teach that polymers having acetoacetyl pendant groups provide for improved adhesion to smooth non-absorbent surfaces. Further, U.S. Pat. No. 5,055,511 and 5,120,607 describe the use of acetoacetylated acrylic polymers in mastic caulking compositions. Other patents, such as U.S. Pat. No. 5,002,998, U.S. Pat. No. 4,292,661, EP 390,370, EP 262,720 and EP 326,723, and Japanese Kokai Hei 4 (1992)-154873 describe the use of polymers containing acetoacetoxy groups bound to the polymeric structure. Further, U.S. Pat. No. 5,349,026 describes the use of a polymer, containing an acetoacetate group, in a coating or impregnating composition. The polymer functions to coalesce and crosslink an emulsion polymer. U.S. Pat. No. 5,494,975 describes preparation of polymers containing functional acetoacetate groups which are then reacted with a functional amine to form an enamine.

European Patent Application 262,720 refers to the use of polymers which contain pendant acetoacetoxy groups as adhesion promoters and further discloses that these polymers protect the acetoacetoxy moieties from hydrolyzing by adding a sufficient amount of ammonia or amine to convert the acetoacetoxy moieties to the corresponding enamines.

In all of the above references, the acetoacetoxy group is chemically bound to the polymer which forms the coating. This severely limits the chemical nature of the polymeric coating, since the polymer must either be based upon an acetoacetylated copolymerizable monomer or it must contain pendant groups, such as hydroxy or amine, which are capable of reacting with an acetoacetylating agent.

Japanese Patent 3,290,486 describes a process for promoting adhesion to a tin-lead alloy plated steel sheet which involves immersing the sheet in an aqueous acetoacetic acid ester prior to painting.

SUMMARY OF THE INVENTION

The present invention provides a method for improving the adhesion of waterborne coating compositions to various substrates, especially to rusty, corroded or galvanized metals. The invention also provides waterborne coating compositions comprising an aqueous polymer dispersion, an enamine component and, optional conventional additives. The waterborne compositions have improved adhesion to substrates, particularly to rusty, corroded and galvanized metal surfaces.

A further aspect of the present invention is the discovery of two novel compounds, 2-butyl-2-ethyl-1,3-propanediol bis(3-amino-2-butenoate) and trimethylpropane tris(3-amino-2-butenoate), which also improve adhesion of waterborne coatings to substrates.

DESCRIPTION OF THE PREFERRED EMBODIMENTS

Applicants have unexpectedly found that when a non-polymeric enamine is added to waterborne coating compositions either as a pure compound or as a solution or as a dispersion, in the presence of other conventional paint additives such as coalescing aids, adhesion of the waterborne coating composition to a substrate is enhanced. Further, the enamine of the present invention may be added to the waterborne composition during formulation of the aqueous polymer composition or just prior to application of the formulation onto a substrate. The resulting waterborne composition has the desirable properties of the base polymer composition, however, in addition, exhibits greatly improved adhesion, especially to corroded metal and oxidized substrates.

Thus, the present invention provides waterborne compositions comprising: (A) an aqueous dispersion polymer, and (B) a compound of formula (I) which is represented by a number of tautomeric and isomeric forms such as:

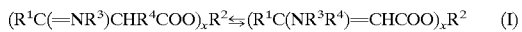

where $R^1$ and $R^2$ are independently $C_1$–$C_5$ alkyl groups or the residue of a polyol, either or both of $R^3$ and $R^4$ are hydrogen or $C_1$–$C_5$ alkyl groups, and x is an integer of from 1 to 3.

Component (A)—Aqueous Dispersion Polymer

Useful aqueous dispersion polymers for practice of the present invention may be selected from an acrylic latex, a vinyl polymer and a water-borne alkyd. Preferably, the aqueous dispersion polymer of the present invention is an acrylic latex polymer or vinyl latex polymer formed by copolymerization of known monoethylenically unsaturated monomers. The term "latex" is used in the conventional meaning to denote stable dispersions of resin particles in a water system. Further, the term "polymer" is used to denote a homopolymer or a copolymer.

Suitable polymerizable or copolymerizable monoethylenically unsaturated monomers for the preparation of a latex polymer include, but are not limited to, a monoethylenically unsaturated monomer which may be represented by the general Formula (II):

where $R^3$ is hydrogen or a $C_1$–$C_3$ alkyl group, and $R^4$ is a $C_1$–$C_{20}$ alkyl group, phenyl, benzyl, hydroxy-($C_1$–$C_4$)-alkyl, alkoxy-($C_1$–$C_4$)-alkyl, cyclopentyl, cyclohexyl, $C_1$–$C_4$-alkylfuryl, tetrahydrofuryl, $C_1$–$C_4$ alkyltetrahydrofuryl and combinations of these monomers thereof. Combinations of monomers where $R^3$ is hydrogen and monomers where $R^3$ is an alkyl group are used to modify the glass transition temperature of the latex polymer.

Preferred examples of comonomers are, but are not limited to, methyl (meth)acrylate, ethyl (meth)acrylate, propyl (meth)acrylate, isopropyl (meth)acrylate, butyl (meth) acrylate, isobutyl (meth)acrylate, hexyl (meth)acrylate, isooctyl (meth)acrylate, isodecyl (meth)acrylate, lauryl (meth)acrylate, stearyl (meth)acrylate, phenoxyethyl (meth) acrylate, methoxyethyl (meth)acrylate, benzyl (meth) acrylate, ethoxyethyl (meth)acrylate, 2-ethylhexyl (meth) acrylate, cyclopentyl (meth)acrylate, and isobornyl (meth) acrylate, as well as combinations of those monomers thereof. The term "(meth)acrylate" is used to denote an acrylate or methacrylate. The term "alkyl" is used to denote straight chain or branched alkyl groups.

Additional suitable monoethylenically unsaturated monomers include styrenic monomers. Styrenic monomers denote styrene, or a substituted styrene, such as $C_1$–$C_6$ alkyl ring-substituted styrene, $C_1$–$C_3$ alkyl-substituted styrene or a combination of ring and -alkyl substituted styrene. Preferred styrenic copolymerizable monomers include styrene, p-methyl styrene, o-methyl styrene, -methyl styrene and combinations thereof.

In addition, vinyl ester monomers may be used as monoethylenically unsaturated monomers. Such vinyl esters include vinyl acetate, di-n-butylmaleate, and compounds of the general Formula (III):

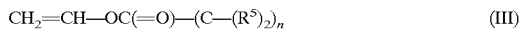

$$CH_2=CH-OC(=O)-(C-(R^5)_2)_n \qquad (III)$$

where $R^5$ is a hydrogen or a $C_1$–$C_{12}$ alkyl group and where n is an integer of 1 to 20; preferably at least one $R^5$ is methyl.

The latex polymers referred to herein are known polymers. Latex polymers can be prepared by conventional free radical emulsion polymerization processes known in the art. Conventional catalysts used in emulsion polymerization include hydrogen peroxide, potassium or ammonium peroxidisulfate, dibenzoyl peroxide, lauryl peroxide, ditertiarybutyl peroxide, 2,2'-azobisisobutyronitrile, t-butyl peroxide, t-butyl hydroperoxide, benzoyl peroxide, sodium formaldehyde sulfoxylate and the like.

Suitable surfactants for the preparation of latex polymers include anionic or nonionic surfactants, such as alkylpolyglycol ethers, including ethoxylation products of lauryl, oleyl, and stearyl alcohols; alkylphenolpolyglycol ethers, such as ethoxylation products of octyl- or nonylphenol, diisopropylphenol, triisopropylphenol; alkali metal ammonium salts or alkyl, aryl or alkylaryl sulfonates, sulfates, phosphates, and the like, including sodium lauryl sulfate, sodium octylphenol glycol ether sulfate, sodium dodecylbenzene sulfonate, sodium lauryl diglycol sulfate, ammonium tri-tertiary butyl phenol sulfonate, and penta- and octa-glycol sulfonates; sulfosuccinate salts such as disodium ethoxylated nonylphenol, half ester or sulfosuccinic acid, disodium n-octyldecyl sulfosuccinate, sodium dioctyl sulfosuccinate, and the like. The term "aryl" in the context of this application is used to denote an aromatic ring radical or a substituted aromatic ring radical, such as phenyl, naphthyl or anthracenyl radical.

In addition, reactive anionic or nonionic surfactants possessing styrene or allyl groups may be used in the preparation of latex polymers. Examples include surface active monomers such as SAM 181, 183, 184, 211, sold by PPG Industries, Inc., which are anionic sulfates or sulfonates, and SAM 185-187 which are nonionic reactive surfactants. Other reactive surfactants include those sold by Daiichi Kogyo Seiyaku under the name AQUARON surfactant. Examples of AQUARON surfactants include compounds of the formulae:

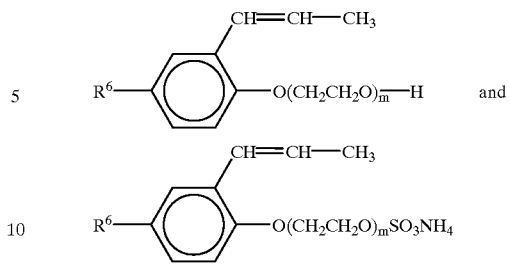

wherein $R^6$ is $C_1$–$C_{12}$ alkyl group and m is an integer of from 1 to 5. Additional reactive surfactants include sodium alkyl allyl sulfosuccinate, sold by Henkel under the tradename TREM LF40 surfactant. Further examples of such surfactants can be found in U.S. Pat. Nos. 5,185,212; 2,600,831; 2,271,622; 2,271,623; 2,275,727; 2,787,604; 2,816,920; and 2,739,891, incorporated herein by reference.

Alternatively, the aqueous suspension polymer can be waterborne alkyds. The term "alkyd" is used to denote a synthetic resin which is the condensation product of polybasic acids, polyhydric alcohols and oil fatty acids. Such alkyds are generally prepared by polycondensation of various polybasic acids, polyhydric alcohols and fatty acids. The term "oil fatty acid" as used herein denotes, for example, tall oil fatty acid (TOFA), linseed oil, soybean oil, coconut oil, castor oil, sunflower oil, safflower oil, tung oil, oiticia oil, etc. These oils contain both saturated and unsaturated fatty acids. Depending on oil type and composition, the saturated fatty acid content varies in the range of from about 2.0 to 95.0 weight %, whereas the unsaturated fatty acid content varies from about 10.0 to about 98.0 wt. %.

The saturated fatty acid content in these oils is mainly from a mixture of stearic ($C_{18}$) and palmitic ($C_{16}$) acids, but various oils containing saturated fatty acids with $C_8$, $C_{10}$, $C_{14}$ carbon chain may also be used. The unsaturated fatty acid content in these oils is mainly from oleic acid, linoleic acid and linolenic acid.

Polyhydric alcohols used in the preparation of waterborne alkyds include glycerol, neopentyl glycol (NPG), cyclohexanedimethanol (CHDM), ethylene glycol, propylene glycol, pentaerythritol, neononyl glycol (NNG), diethylene glycol (DEG), dipropylene glycol (DPG), trimethyl pentanediol (TMPD), triethylene glycol (TEG), trimethylolpropane (TMP), dipentaerythritol (DPE), tripentaerythritol (TPE) and the like.

Polybasic acids used in the preparation of waterborne alkyds include, but are not limited to, cyclohexanedicarboxylic acid (CHDA), isophthalic acid (IPA), terephthalic acid (TPA), phthalic anhydride (PA), adipic acid (AD), oxalic acid, malonic acid, dimethylmalonic acid, succinic acid, glutaric acid, trimethyladipic acid, pimelic acid, 2,2-dimethylglutaric acid, azelaic acid, sebacic acid, fumaric acid, maleic acid, itaconic acid, 2,5-norbornane dicarboxylic acid, 1,4-naphthalic acid, diphenic acid, 4,4'-oxydibenzoic acid, diglycolic acid, thiodipropionic acid, 4,4'-oxydibenzoic acid, diglycolic acid, thiodipropionic acid, 4,4'-sulfonyldibenzoic acid, 4,4'-diphenyldicarboxylic acid, and 2,6-naphthalene dicarboxylic acid. Suitable dicarboxylic acids used in waterborne alkyds include aliphatic dicarboxylic acids, aromatic dicarboxylic acids, alicyclic dicarboxylic acids or mixtures of two or more of these acids. Examples of commercially available waterborne alkyds include AROLON resin, available from Reichhold. Further examples may be found in the treatise by C. R. Martens, in "Alkyd Resins", Reinhold Publishing Corp., New York, 1961.

Acetoacetate compounds useful in the practice of the present invention may be prepared by methods known in the art, such as those described in U.S. Pat. No. 5,051,529, incorporated herein by reference.

In the above described waterborne compositions, the aqueous dispersion polymer may preferably have a particle size of from about 0.01 to about 3 microns, as measured by electron microscopy. The polymer particles generally have a spherical shape. In a preferred embodiment, the spherical polymeric particle has a core portion and a shell portion or a gradient structure. Conventionally, in core/shell particles the Tg of the polymer composition of the core is different from the Tg of the polymer composition of the shell. The core/shell polymer particles may also be prepared in a multi-lobe form, a peanut shell, an acorn form, a raspberry form or any other form.

The glass transition temperature (Tg) of the aqueous dispersion polymer, in accordance with the present invention, may be up to about 100° C. In a preferred embodiment of the present invention, where film forming at ambient temperatures is desirable, the glass transition temperature may preferably be under 60° C.

It should be understood that the only limitation on the aqueous dispersion polymer is that it is one in which the polymer contains no functional groups which are reactive with component (B), an enamine. It is preferred that the polymer component (A) does not contain a pendant functionality or formula of an enamine, either by copolymerization with a monomer containing such functionalities or by a post reaction to introduce pendant acetoacetate functionalities of formula (IV):

$$—(R^1C(=O)CH_2COO)_xR^2 \qquad (IV)$$

where $R^1$, $R^2$ and x are as defined in formula (I), which might react to form an enamine.

Component (B)—Enamine Compound

Component (B) is an enamine which is not chemically bound to the aqueous polymer dispersion (A). Component (B) is a compound represented by formula (I):

$$(R^1C(NR^3R^4)=CHCOO)_xR^2 \qquad (I)$$

It is further understood that formula (I) may exist in the following form:

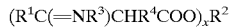

$$(R^1C(=NR^3)CHR^4COO)_xR^2$$

Thus, formula (I) represents both tautomeric and isomeric forms of an enamine. The term "enamine" is used to denote a reaction product of an acetoacetic acid ester with a primary or secondary amine according to the following equation

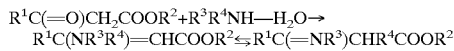

$$R^1C(=O)CH_2COOR^2+R^3R^4NH \longrightarrow{-H_2O}$$
$$R^1C(NR^3R^4)=CHCOOR^2 \leftrightarrows R^1C(=NR^3)CHR^4COOR^2$$

where $R^1$ and $R^2$ are $C_1$–$C_5$ alkyl groups as defined above and either or both $R^3$ and $R^4$ are hydrogen or the same or different $C_1$–$C_5$ alkyl groups. Further, if the amine is primary, $R^4$ is hydrogen and the reaction product may exist in either of the tautomeric forms shown in the above equation. On the other hand the reaction product of a secondary amine exists only in the enamine form.

Preferred compounds of Formula (I) include, but are not limited to, enamines of acetoacetate esters such as: the enamine of ethylene glycol bis(acetoacetate); the enamine of diethylene glycol bis(acetoacetate); the enamine of propylene glycol bis(acetoacetate); the enamine of 2,2,4-trimethylene glycol bis(acetoacetate); the enamine of cyclohexanediol bis(acetoacetate); the enamine of trimethylpropane tris(acetoacetate) and the enamine of glycerol tris(acetoacetate). Limitations of $R^1$ and $R^2$ are chiefly those imposed by the physical characteristics such as melting point, volatility, solubility, etc., of the resulting ester. Examples of such compounds include, but are not limited to, those where $R^1$ is methyl, $R^2$ is t-butyl, and x is 1; where $R^1$ is methyl, $R^2$ is ethyl and x is 1; and where $R^1$ is ethyl, $R^2$ is butyl and x is 1. Further, either or both of $R^1$ and $R^2$ may contain other substituents, so long as component (B) contains no substituents that are reactive with component (A) to which they are added and does not adversely affect the substrate to which they are applied.

The amount of component (B) required to produce the desired adhesion promoting effect will depend upon a number of factors, such as the degree of corrosion of the metal substrate or other pretreatment to which the substrate has been subjected. In general, the preferred range is from 1 to 25 parts by weight of component (B) per 100 parts by weight (phr) of aqueous polymer dispersion component (A); a more preferred range is from 10 to 25 phr; and most preferred is from 15 to 20 phr. The upper concentration of component (B) may be limited both by economic considerations and because incremental improvement may be slight at concentrations of component (B) above about 25 phr.

In a further aspect of the present invention, where the acetoacetate ester is derived from 2-butyl-2-ethyl-1,3-propane diol or from trimethylpropane, and the amine is ammonia, the products, namely, 2-butyl-2-ethyl-1,3-propanediol bis(3-amino-2-butenoate) and trimethylpropane tris(3-amino-2-butenoate), respectively, are new compositions of matter useful in the present invention for promoting adhesion of waterborne compositions to various substrates.

Component C—Additives

Components (A) and (B) of this invention may be used in combination with other optional conventional paint additives, such as coalescing aids, dryers, pigments, surfactants, and the like.

Included among such additives are leveling, rheology, and flow control agents such as silicones, fluorocarbons or cellulosics; flatting agents; pigment wetting and dispersing agents and surfactants; ultraviolet (UV) absorbers; UV light stabilizers; tinting pigments; defoaming and antifoaming agents; anti-settling, anti-sag and bodying agents; anti-skinning agents; anti-flooding and anti-floating agents; fungicides and mildewcides; corrosion inhibitors; thickening agents; or coalescing agents.

Specific examples of such additives can be found in "Raw Materials Index", published by the National Paint & Coatings Association, 1500 Rhode Island Avenue, N.W., Washington, D.C. 20005.

Examples of flatting agents include SYLOID® synthetic silica, available from the Davison Chemical Division of W.R. Grace & Company; HERCOFLAT® polypropylene, available from Hercules Inc.; and ZEOLEX® synthetic silicate, available from J.M. Huber Corporation.

Examples of dispersing agents and surfactants include sodium bis(tridecyl) sulfosuccinnate, di(2-ethyl hexyl) sodium sulfosuccinnate, sodium dihexylsulfosuccinnate, sodium dicyclohexyl sulfosuccinnate, diamyl sodium sulfosuccinnate, sodium diisobutyl sulfosuccinnate, disodium iso-decyl sulfosuccinnate, disodium ethoxylated alcohol half ester of sulfosuccinnic acid, disodium alkyl amido polyethoxy sulfosuccinnate, tetrasodium N-(1,2-dicarboxyethyl)-N-oxtadecyl sulfosuccinnamate, disodium N-octasulfosuccinnamate, sulfated ethoxylated nonylphenol, 2-amino-2-methyl-1-propanol, and the like.

Examples of viscosity, suspension, and flow control agents include polyaminoamide phosphate, high molecular weight carboxylic acid salts of polyamine amides, and alkylene amine salts of an unsaturated fatty acid, all available from BYK Chemie U.S.A. under the tradename ANTI TERRA® wetting agent. Further examples include polysiloxane copolymers, aqueous polyacrylate solution, cellulose esters, hydroxyethyl cellulose, hydrophobically-modified hydroxyethyl cellulose, hydroxypropyl cellulose, polyamide wax, polyolefin wax, carboxymethyl cellulose, ammonium polyacrylate, sodium polyacrylate, and polyethylene oxide. Examples of thickeners include the methane ethylene oxide associative thickeners and water soluble carboxylated thickeners, for example, UCAR 45 water soluble carboxylated thickener available from by Union Carbide.

Several proprietary antifoaming agents are commercially available, for example, under the tradename BRUBREAK of Buckman Laboratories Inc., under the BYK® tradename of BYK Chemie, U.S.A., under the FOAMASTER® and NOPCO® tradenames of Henkel Corp./Coating Chemicals, under the DREWPLUS® tradename of the Drew Industrial Division of Ashland Chemical Company, under the TROYSOL® and TROYKYD® tradenames of Troy Chemical Corporation, and under the SAG® tradename of Union Carbide Corporation.

Examples of fungicides, mildewcides, and biocides include 4,4-dimethyloxazolidine, 3,4,4-trimethyloxazolidine, modified barium metaborate, potassium N-hydroxy-methyl-N-methyldithiocarbamate, 2-(thiocyanomethylthio)benzothiazole, potassium dimethyl dithiocarbamate, adamantane, N-(trichloromethylthio) phthalimide, 2,4,5,6-tetrachloroisophthalonitrile, orthophenyl phenol, 2,4,5-trichlorophenol, dehydroacetic acid, copper naphthenate, copper octoate, organic arsenic, tributyl tin oxide, zinc naphthenate, and copper 8-quinolinate.

Further, examples of useful conventional additives (C) can be found in "Raw Materials Index", published by the National Paint & Coatings Association, 1500 Rhode Island Avenue, N.W., Washington, D.C. 20005.

Examples of U.V. absorbers and U.V. light stabilizers include substituted benzophenone, substituted benzotriazoles, hindered amines, and hindered benzoates, available from American Cyanamide Company under the tradename CYASORB UV, and diethyl-3-acetyl-4-hydroxybenzyl-phosphonate, 4-dodecyloxy-2-hydroxy benzophenone, and resorcinol monobenzoate.

The paint or coating additives described above form a relatively minor proportion of the waterborne composition of the present invention, Additive component (C) may be present in an amount from about 0.05 wt. % to about 5.00 wt. %, based on the total weight of components (A) and (B) of the waterborne composition. However, the amount of additives is not critical and may be adjusted higher or lower to obtain desired properties.

The waterborne composition as set forth above, may further comprises one or more pigments in a concentration of about 1 to about 70 wt. %, preferably about 30 to about 60 wt. % based on the total weight of components (A) and (B) in the waterborne composition.

Pigments suitable for use in the coating compositions envisioned by the present invention are typically organic and inorganic pigments, well-known to one of ordinary skill in the art of surface coatings. Examples include, but are not limited to the following: CI Pigment White 6 titanium dioxide; CI Pigment Red 101 red iron oxide; CI Pigment Yellow 42, CI Pigment Blue 15, 15:1, 15:2, 15:3, 15:4, all copper phthalocyanines; CI Pigment Red 49:1; and CI Pigment Red 57:1.

After formulation, the waterborne composition may then be applied to a desired substrate or article, e.g., steel, aluminum, or galvanized sheeting (either primed or unprimed), and allowed to air dry. A waterborne composition in accordance with the present invention may further be designed for industrial coatings, textile coatings, ink coatings, adhesives, or coatings for plastics. While the compositions of the invention are preferentially applied as coatings for rusty or corroded metal substrates, it should be understood that the waterborne coating compositions are adhesion promoters and may also be broadly applicable to other substrates. Thus, as a further aspect of the present invention, there is provided a method for coating a shaped or formed article with the waterborne compositions of the present invention.

Although the invention is described in the Examples that follow particularly with reference to rusted or Bonderized™ steel, it should be understood that they are also applicable to cleaned and treated metal or to metal which has been subjected to other treatments, such as galvanizing or treating with other surface coatings. Use of the composition of the present invention on various iron alloys, in addition to steel, is also within the scope of the present invention.

Having generally described this invention, a further understanding can be obtained by reference to certain specific examples which are provided herein for purposes of illustration only and are not intended to be limiting unless otherwise specified.

EXAMPLES

Test Methods
Metal Pretreatment

Cold rolled steel was used as the substrate in all of the examples. Unless specified otherwise, the steel was subjected to treatment with BONDERITE™ 1000 iron phosphate wash. For evaluation on "rusted" steel, cold rolled steel was "rusted" by treatment in a salt fog chamber for 96 hours and washed to remove traces of salt.

Adhesion to Substrates

Adhesion was evaluated by the "Cross-Cut Tape Test" described in ASTM 3359-87, "Standard Test Methods for Measuring Adhesion by Tape Test", using a Gardner Cross Hatch Adhesion Tester. The grid was covered with pressure sensitive tape, which was smoothed by hand to ensure good contact, and then removed by a rapid pulling motion. The degree of adhesion of the coating was rated from the damage to the grid and reported in the following tables as percentage of paint squares which remained intact.

Salt Fog Test

This test was run according to ASTM Method B117-90, in which salt fog was allowed to deposit on the test paneling in a closed chamber, after which the panel was examined visually and, if desired, subjected to other tests.

Component (A)—Aqueous Dispersion Polymer

The following resins were used in the examples: NEOCRYL® acrylic-styrene resin, a registered trade mark of ICI; RHOPLEX® acrylic resin, a registered trade mark of Rohm and Haas; and AROLON® water dispersible alkyd resin, a registered trade mark of Reichhold.

Example 1

This example illustrates the preparation of the "enamine", 2-butyl-2-ethyl-1,3-propanediol bis(3-amino-2-butenoate).

Aqueous ammonium hydroxide (9.54 g of 28% solution) was added drop wise, with stirring, to 3 g of 2-butyl-2-ethyl-1,3-propanediol and the resulting mixture was stirred vigorously for about 2 minutes, then allowed to stand for 48 hours. The product consisted of an oily top layer, a lower aqueous layer, and a milky precipitate. The product was extracted with methylene chloride and the organic layer washed with saturated sodium chloride. The methylene chloride was removed by heating on a rotary evaporator at 50° C. at 100 mm for 2 hours. Analysis of the product by $H^1$ NMR indicated that it contained the mono- and di-enamines of 2-butyl-2-ethyl-1,3-propanediol bis(3-amino-2-butenoate).

Example 2

The above reaction was carried out using trimethylol propane tris(acetoacetate) to similarly yield trimethylolpropane tris(3-amino-2-butenoate), the identity of which was confirmed by $H^1$NMR.

Example 3

This example illustrates the preparation of ethyl 3-amino-2-butenoate and its use as an adhesion promoter.

A mixture of 60 g of ethyl acetoacetate and 222 g of ammonium hydroxide was shaken vigorously in a separatory funnel and the resulting lower, oil, layer of ethyl 3-amino-2-butenoate was removed. This material (5 g) was then added to 50 g of NEOCRYL® A650 acrylicstyrene resin, with the pH adjusted to about 9.8 by addition of ammonium hydroxide. The mixture was placed on a roller for 8 hours to mix thoroughly, then coated onto Bonderite™ 1000 cold rolled steel panels to give approximately 3 mil films. After curing the coating was evaluated by the cross hatch adhesion test described above. The film showed 100% retention of the coating. In contrast, a control film of NEOCRYL® A650 acrylic-styrene resin, which did not contain the enamine, showed 0% retention of the coating.

Example 4

An identical experiment described in Example 3 was carried out using tertiary butyl-3-amino-2-butenoate. The film showed 100% retention of the coating.

Example 5

This example illustrates the use of ethyl-3-amino-2-butanoate to improve the adhesion of a waterborne epoxy enamel, an enamel which normally exhibits poor early adhesion to steel.

An epoxy enamel was used as received from the manufacturer and contained TRU-GLAZE™ epoxy #12949-01 and #12902-01. A sample of this material was mixed with a small amount of ethyl 3-amino-2-butenoate and the product was coated onto Bonderite™ 1000 treated cold rolled steel and cured for 3 hours at 50° C. The resulting coating showed 100% retention of the coating in the cross hatch adhesion test described above. In contrast, a similar coating made from the enamel without added enamine showed less than 50% retention of the coating.

Example 6

This example illustrates the preparation of coatings utilizing the acetoacetate enamine as a hydrolytically stable form of acetoacetate for adhesion promotion.

Coating compositions were prepared according to Table 1 below. The coating compositions containing the waterborne latex were placed on a roller for 8 hours to mix, then coated onto Bonderite™ 1000 cold rolled steel to give about 3 mil wet films. After curing, the coatings were evaluated by the cross hatch adhesion test described above. These results are shown in Table 2. All the films of the present invention showed 100% initial retention to the substrate. The coated samples were then placed in an oven at 50° C. for 4 weeks, after which they were reevaluated for adhesion. These results are also shown in Table 2.

TABLE 1

COATINGS COMPOSITIONS

| Components | A | B | C | D | E | F |
|---|---|---|---|---|---|---|
| Neocryl A650 with NH$_4$OH (pH = 9.8)* | 50 g | 50 g | 50 g | — | — | — |
| Neocryl A650 (pH = 6.3) | — | — | — | 50 g | 50 g | 50 g |
| ethyl acetoacetate | — | — | — | 5.6 g | — | — |
| t-butyl acetoacetate | — | — | — | — | 5.6 g | — |
| BEPD bis acetoacetate | — | — | — | — | — | 5.6 |
| EAA enamine | 5.0 g | — | — | — | — | — |
| t-BAA enamine | — | 5.0 g | — | — | — | — |
| BEPD bis enamine | — | — | 5.0 g | — | — | — |

BEPD = 2-butyl-2-ethyl-1,3-propane diol
EAA = Ethyl acetoacetate
t-BAA = t-butyl acetoacetate
*NEOCRYL A650 has a pH of about 6.5. Ammonium hydroxide was used to adjust the pH to 9.8 to help keep the acetoacetate enamine in the enamine form.
All aceotoacetates (enamine or otherwise) were added at 25 parts by weight per 100 parts of resin solids.

TABLE 2

EVALUATION AND STABILITY OF COATINGS

| Components | Initial Cross Hatch Adhesion Results | Final (4 Wks) Cross Hatch Adhesion Results |
|---|---|---|
| Neocryl A650 NH$_4$OH (pH = 9.8 | 0% | 0% |
| Neocryl A650 (pH = 6.3)* | 0% | 0% |
| Ethyl Acetoacetate | 100% | 0% |
| t-Butyl Acetoacetate | 100% | 100% |
| BEPD bis Acetoacetate | 100% | Gelled |
| EAA Enamine | 100% | 100% |
| t-BAA Enamine | 100% | 100% |
| BEPD bis Enamine | 100% | 100% |

*EKTASOLVE EB at 25 phr was used to coalesce the film.
BEPD = 2-butyl-2-ethyl-1,3-propane diol
EAA = ethyl acetoacetate
t-BAA = t-butyl acetoacetate The results show adhesion to the substrate remained at 100% retention for both the acetoacetate and enamine forms of both tertiary butyl acetoacetate and 2-butyl-2-ethyl-1,3-propane diol. The other acetoacetates showed loss of adhesion Example 7

The latex coating formulations of Example 6 were observed for stability after 4 weeks storage in an oven at 50° C. The observations are shown below in Table 3.

TABLE 3

STORAGE STABILITY STUDY AT 50° C.

| Components | Stability Observations |
|---|---|
| Neocryl A650 NH₄OH (pH = 9.8 | None Expected |
| Neocryl A650 (pH = 6.3)* | None Expected |
| Ethyl Acetoacetate | Popped and Fizzed When Opened |
| t-Butyl Acetoacetate | Popped and Fizzed When Opened |
| BEPD bis Acetoacetate | No Change Noted |
| EAA Enamine | Solid Lump in Liquid |
| t-BAA Enamine | No Change Noted |
| BEPD bis Enamine | No Change Noted |

*EKTASOLVE EB at 25 phr was used to coalesce the film.
BEPD = 2-butyl-2-ethyl-1,3-propane diol
EAA = ethyl acetoacetate
t-BAA = t-butyl acetoacetate After 4 weeks aging, the latex compositions containing 2-butyl-2-ethyl-1,3-propane diol bis acetoacetate and the enamine form of 2-butyl-2-ethyl-1,3-propane diol bis acetoacetate, along with the t-butyl acetoacetate enamine, did not exhibit the characteristic "pop and fizz" or the odor of a ketone when opened. In contrast, the other non-enamine acetoacetates, stored under the same conditions, did exhibit the characteristic "pop and fizz" and ketone odor when opened, indicating hydrolysis had occurred. The ethyl acetoacetate enamine destabilized the emulsion in this test.

Obviously, numerous modifications and variations of the present invention are possible in light of the above teachings. It is therefore to be understood that within the scope of the appended claims, the invention may be practiced otherwise than as specifically described herein.

What is claimed is:

1. The compound 2-butyl-2-ethyl-1,3-propanediol bis(3-amino-2-butenoate).

2. The compound trimethylpropane tris(3-amino-2-butenoate).

* * * * *